(12) United States Patent
Cheruvallath et al.

(10) Patent No.: US 10,328,089 B2
(45) Date of Patent: Jun. 25, 2019

(54) FUMAGILLOL DERIVATIVES

(71) Applicant: Takeda Pharmaceutical Company Limited, Osaka (JP)

(72) Inventors: Zacharia Cheruvallath, San Diego, CA (US); John David Lawson, Carlsbad, CA (US); Christopher McBride, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/796,519

(22) Filed: Oct. 27, 2017

(65) Prior Publication Data

US 2018/0050051 A1    Feb. 22, 2018

Related U.S. Application Data

(62) Division of application No. 14/974,033, filed on Dec. 18, 2015, now Pat. No. 9,827,255.

(60) Provisional application No. 62/094,823, filed on Dec. 19, 2014.

(51) Int. Cl.

| | | |
|---|---|---|
| A61K 31/665 | (2006.01) | |
| A61K 31/683 | (2006.01) | |
| A61K 45/06 | (2006.01) | |
| C07F 9/6558 | (2006.01) | |
| A61K 31/66 | (2006.01) | |
| A61K 38/28 | (2006.01) | |
| A61K 31/155 | (2006.01) | |
| A61K 31/192 | (2006.01) | |
| A61K 31/216 | (2006.01) | |
| A61K 31/336 | (2006.01) | |
| A61K 31/397 | (2006.01) | |
| A61K 31/4985 | (2006.01) | |
| A61K 31/662 | (2006.01) | |
| A61P 3/10 | (2006.01) | |
| A61K 31/64 | (2006.01) | |

(52) U.S. Cl.
CPC ......... *A61K 31/665* (2013.01); *A61K 31/155* (2013.01); *A61K 31/192* (2013.01); *A61K 31/216* (2013.01); *A61K 31/336* (2013.01); *A61K 31/397* (2013.01); *A61K 31/4985* (2013.01); *A61K 31/64* (2013.01); *A61K 31/66* (2013.01); *A61K 31/662* (2013.01); *A61K 31/683* (2013.01); *A61K 38/28* (2013.01); *A61K 45/06* (2013.01); *A61P 3/10* (2018.01); *C07F 9/65586* (2013.01)

(58) Field of Classification Search
CPC .... A61K 31/665; A61K 31/155; A61K 31/66; A61K 31/662; A61K 31/64; A61K 31/4985; A61K 31/397; A61K 31/336; A61K 31/683; A61K 31/192; A61K 31/216; A61K 45/06; A61K 38/28; A61K 2300/00; C07F 9/65586; A61P 3/10
See application file for complete search history.

(56) References Cited

U.S. PATENT DOCUMENTS

| | | | |
|---|---|---|---|
| 6,063,812 A * | 5/2000 | Hong, II | C07D 303/22 514/475 |
| 6,306,819 B1 | 10/2001 | Rupnick et al. | |
| 6,949,584 B2 | 9/2005 | Satchi-Fainaro et al. | |
| 9,827,255 B2 | 11/2017 | Cheruvallath et al. | |
| 2002/0151493 A1 | 10/2002 | Arico-Muendel et al. | |
| 2008/0200402 A1 | 8/2008 | Alvinerie et al. | |
| 2010/0056623 A1* | 3/2010 | Lee | C07D 303/28 514/475 |
| 2012/0004162 A1 | 1/2012 | Vath | |
| 2012/0034233 A1 | 2/2012 | Hughes et al. | |

FOREIGN PATENT DOCUMENTS

| | | |
|---|---|---|
| EP | 0354787 | 2/1990 |
| EP | 359036 A1 | 3/1990 |
| WO | 98/56372 | 12/1998 |
| WO | WO 99/39702 | 8/1999 |

(Continued)

OTHER PUBLICATIONS

D. Ingber et al., Nature 348:555-57 (1990).
E.C. Griffith et al., Chemistry & Biology 4(6):461-471 (1997).
M.A. Rupnick et al., Proc. Natl. Acad. Sci. USA 99(16):10730-35 (2002).
E Bråkenhielm, et al., Circulation Research 94(12):1579-88 (2004).
H.R. Lijnen et al., Obesity 18(12):2241-46 (2010).
Y.M. Kim, et al., J. Mol. Endocrinology, 38:455-65 (2007).
M. Leszczyniecka et al., Oncogene 25:3471-78 (2006).
S.M. Arfin et al., Proc. Natl. Acad. Sci. USA 92:7714-18 (1995).
R.S. Herbst et al., J. Clin. Oncology 20(22):4440-47 (2002).
C.J. Logothetis et al., Clin. Cancer Res. 7:1198-1203 (2001).

(Continued)

*Primary Examiner* — Blessing M Fubara
(74) *Attorney, Agent, or Firm* — Matthew J. Russo

(57) ABSTRACT

Disclosed are compounds of Formula 1,

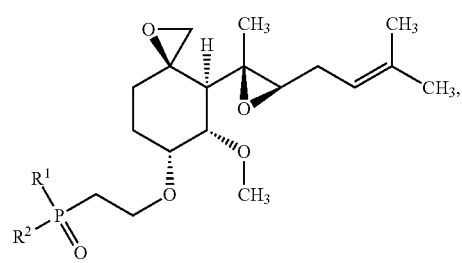

stereoisomers thereof and pharmaceutically acceptable salts of the compounds and stereoisomers, wherein $R^1$ and $R^2$ are defined in the specification. This disclosure also relates to materials and methods for preparing compounds of Formula 1, to pharmaceutical compositions which contain them, and to their use for treating obesity and related diseases, disorders, and conditions associated with MetAP2.

35 Claims, No Drawings

(56) References Cited

FOREIGN PATENT DOCUMENTS

| WO | WO 99/59986 | * 11/1999 |
| --- | --- | --- |
| WO | WO 99/59987 | 11/1999 |
| WO | 2002/042295 | 5/2002 |
| WO | WO 2003/027104 | 4/2003 |
| WO | WO 2005/082349 | 9/2005 |
| WO | 2009/073445 | 6/2009 |
| WO | 2009/117902 | 10/2009 |
| WO | 2010/065877 | 6/2010 |
| WO | 2010/065883 | 6/2010 |
| WO | WO 2011/130674 | 10/2011 |
| WO | 2011/150338 | 12/2011 |
| WO | WO 2012/122264 | 9/2012 |
| WO | WO 2012/130906 | 10/2012 |

OTHER PUBLICATIONS

W.M. Stadler et al., J. Clin. Oncology 17(8):2541-45 (1999).
A.P. Kudelka et al, N. Engl. J. Med. 338:991-92 (1998).
A.P. Kudelka et al., Clin. Cancer Res. 3:1501-05 (1997).
P. Bhargava et al., Clin. Cancer Res. 5:1989-95 (1999).
W. N. Khan et al., Immunity 3(3): 283-99 (1995).
I. Scroyen et al., Biochimica et Biophysica Acta 1800: 425-29 (2010).
P. Selvakumar, Biochimica et Biophysica Acta 1765: 148-54 (2006).

* cited by examiner

FUMAGILLOL DERIVATIVES

FIELD OF THE INVENTION

This invention relates to fumagillol derivatives, and more particularly to phosphine oxide and phosphonate fumigillol derivatives, which are inhibitors of methionine aminopeptidase 2 (MetAP2), to pharmaceutical compositions which contain them, and to their use to treat diseases, disorders, and conditions associated with MetAP2, including obesity.

BACKGROUND OF THE INVENTION

Methionine aminopeptidases are enzymes that bind to cobalt and manganese ions. The metalloenzymes are widely found in prokaryotic and eukaryotic cells, and exist in three forms, MetAP1A, MetAP1D, and MetAP2. See M. Leszczyniecka et al., *Oncogene* 25:3471-78 (2006). They are responsible for the removal of the N-terminal methionine residue from nascent proteins, an important step in protein maturation and likely essential for proper functional regulation, intracellular targeting, and protein turnover. See S. M. Arfin et al., *Proc. Natl. Acad. Sci. USA* 92:7714-18 (1995). Known (irreversible) inhibitors of MetAP2 include the natural product fumagillin and its more potent semi-synthetic analog TNP-470 (AGM-1470). See D. Ingber et al., *Nature* 348:555-57 (1990); see also E. C. Griffith et al., *Chemistry & Biology* 4(6):461-471 (1997). Both compounds inhibit angiogenesis, and TNP-470 has been evaluated in numerous clinical trials as a treatment for cancer. See, e.g., R. S. Herbst et al., *J. Clin. Oncology* 20(22):4440-47 (2002) (non-small cell lung cancer); C. J. Logothetis et al., *Clin. Cancer Res.* 7:1198-1203 (2001) (progressive androgen-dependent prostate cancer); W. M. Stadler et al., *J. Clin. Oncology* 17(8): 2541-45 (1999) (metastatic renal carcinoma); A. P. Kudelka et al, *N. Engl. J. Med.* 338:991-92 (1998) (metastatic cervical cancer); A. P. Kudelka et al., *Clin. Cancer Res.* 3:1501-05 (1997) (squamous cell cancer of the cervix); and P. Bhargava et al., *Clin. Cancer Res.* 5:1989-95 (1999) (sarcoma, colorectal cancer, and melanoma).

Numerous studies also suggest MetAP2 inhibitors may be used to treat obesity. For example, TNP-470 was tested in various mice obesity models and showed dose-dependent, reversible weight reduction and adipose tissue loss. See M. A. Rupnick et al., *Proc. Natl. Acad. Sci. USA* 99(16):10730-35 (2002). TNP-470 has also been shown to prevent diet-induced obesity in mice. See E. Brakenhielm, et al., *Circulation Research* 94(12):1579-88 (2004). Treatment with fumagillin has been shown to impair diet-induced obesity in mice, as evidenced by adipocyte hypotrophy, but without significantly affecting adipose tissue angiogenesis. See H. R. Lijnen et al., *Obesity* 18(12):2241-46 (2010). Furthermore, a MetAP2 inhibitor, CKD-732, was found to decrease food intake, body weight, fat mass, and the size of adipocytes in genetically and diet-induced obese mice. See Y. M. Kim, et al., *J. Mol. Endocrinology*, 38:455-65 (2007). Recently, CKD-732 (beloranib hemioxalate) has undergone early-phase clinical testing in adult obese patients (e.g., $30 \leq BMI \leq 45$ kg/m$^2$).

Some inhibitors of MetAP2 are described in WO 2012/130906 A1, WO 2012/122264 A1, US 2012/004162 A1, WO 2010/065877 A2, WO 2010/065883 A2, WO 2009/117902 A1, WO 2009/073445 A2, WO 2003/027104 A1, WO 2002/042295 A2, US 2002/0151493 A1, U.S. Pat. No. 6,949,584 B2, WO 99/59987 A1, WO 99/59986 A1, WO 98/56372 A1, EP 0359036 A1, and EP 0354787 A1.

SUMMARY OF THE INVENTION

This invention provides fumagillol derivatives and pharmaceutically acceptable salts thereof. This invention also provides pharmaceutical compositions that contain the fumagillol derivatives and provides for their use to treat diseases, disorders and conditions associated with MetAP2 inhibition, including obesity.

One aspect of the invention provides compounds of Formula 1:

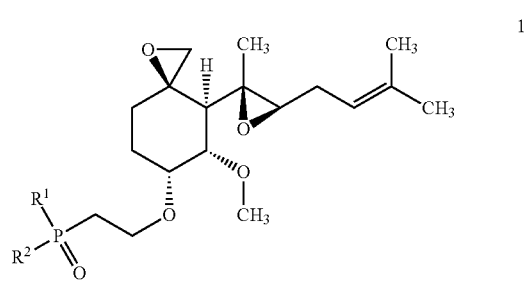

a stereoisomer thereof or a pharmaceutically acceptable salt of the compound or stereoisomer, wherein:

$R^1$ and $R^2$ are each independently selected from phenyl, $C_{3-5}$ heteroaryl, —OR$^4$, and —N(R$^4$)R$^5$, wherein each phenyl and $C_{3-5}$ heteroaryl is independently substituted with from 0 to 3 R$^a$, and each $C_{3-5}$ heteroaryl has 5 or 6 ring atoms of which 1 or 2 are heteroatoms independently selected from N, O, and S;

each R$^a$ is independently selected from halo, —CN, R$^3$, and R$^4$;

each R$^3$ is independently selected from —OR$^4$, —N(R$^4$)R$^5$, —NR$^4$C(O)R$^6$, —NR$^4$C(O)OR$^5$, —C(O)OR$^4$, —C(O)N (R$^4$)R$^5$, —C(O)N(R$^4$)OR$^5$, —C(O)N(R$^4$)S(O)$_2$R$^6$, —N(R$^4$)S(O)$_2$R$^6$, —SR$^4$, —S(O)R$^6$, —S(O)$_2$R$^6$, and —S(O)$_2$N(R$^4$)R$^5$;

each R$^4$ and R$^5$ is independently selected from
 (a) $C_{1-6}$ alkyl, $C_{2-6}$ alkenyl, and $C_{2-6}$ alkynyl, each substituted with from 0 to 3 R$^b$, and
 (b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each substituted with from 0 to 3 R$^c$;

each R$^6$ is independently selected from
 (a) $C_{1-6}$ alkyl, which is substituted with from 0 to 3 R$^b$, and
 (b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each substituted with from 0 to 3 R$^d$;

each R$^b$ is independently selected from halo, —CN, and R$^7$;
each R$^c$ is independently selected from
 (a) halo, —CN, and R$^7$, and
 (b) $C_{1-6}$ alkyl, $C_{2-6}$ alkenyl, and $C_{2-6}$ alkynyl, each substituted with from 0 to 3 R$^b$;

each R$^d$ is independently selected from
 (a) halo, —CN, and R$^7$, and
 (b) $C_{1-6}$ alkyl, which is substituted with from 0 to 3 R$^b$;

each R$^7$ is independently selected from —OR$^8$, —N(R$^8$)R$^9$, —NR$^8$C(O)R$^9$, —NR$^8$C(O)OR$^9$, —C(O)OR$^8$, —C(O)N (R$^8$)R$^9$, —C(O)N(R$^8$)OR$^9$, —C(O)N(R$^8$)S(O)$_2$R$^9$, —N(R$^8$)S(O)$_2$R$^9$, —SR$^8$, —S(O)R$^8$, —S(O)$_2$R$^8$, and —S(O)$_2$N(R$^8$)R$^9$;

each $R^8$ and $R^9$ is independently selected from $C_{1-6}$ alkyl, $C_{3-8}$ cycloalkyl-$(CH_2)_m$—, and $C_{2-6}$ heterocyclyl-$(CH_2)_m$—, each substituted with from 0 to 3 substituents independently selected from halo and —CN; and each m is independently selected from 0, 1, 2, 3, and 4;

wherein each heteroaryl moiety listed in $R^4$, $R^5$, and $R^6$ independently has from 1 to 4 heteroatoms independently selected from N, O, and S, and each heterocyclyl moiety listed in $R^4$, $R^5$, $R^6$, and $R^8$ independently has from 1 to 4 heteroatoms independently selected from N, O, and S.

Another aspect of the invention provides a compound which is selected from the following compounds:

(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)diphenylphosphine oxide;

(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)di-p-tolylphosphine oxide;

(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)bis(4-(trifluoromethyl)phenyl)phosphine oxide;

dimethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate;

diethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate;

a stereoisomer of any one of the aforementioned compounds; and a pharmaceutically acceptable salt of any one of the aforementioned compounds or stereoisomers A further aspect of the invention provides a compound which is represented by the structure:

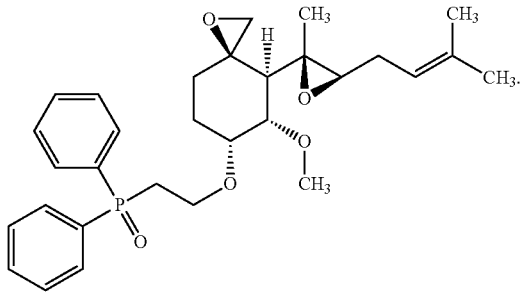 [SMILES: CO[C@@H]1[C@H](OCCP(=O)(c2ccccc2)c2ccccc2)CC[C@]2(CO2)[C@H]1[C@@]1(C)O[C@@H]1CC=C(C)C]

An additional aspect of the invention provides a compound which is represented by the structure:

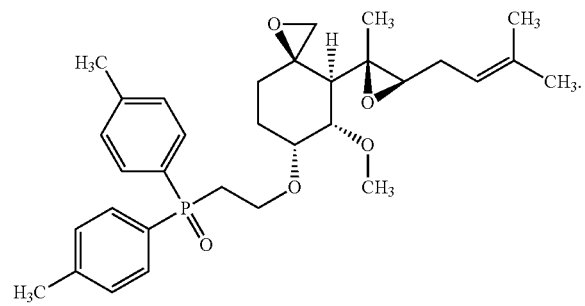 [SMILES: CO[C@@H]1[C@H](OCCP(=O)(c2ccc(C(F)(F)F)cc2)c2ccc(C(F)(F)F)cc2)CC[C@]2(CO2)[C@H]1[C@@]1(C)O[C@@H]1CC=C(C)C]

Another aspect of the invention provides a compound which is represented by the structure:

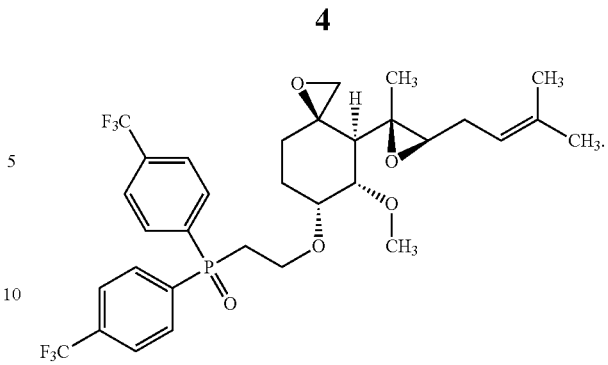

A further aspect of the invention provides a compound which is represented by the structure:

An additional aspect of the invention provides a compound which is represented by the structure:

Another aspect of the invention provides a pharmaceutical composition which includes a compound of Formula 1, a stereoisomer thereof or a pharmaceutically acceptable salt of the compound or stereoisomer, or any one of the compounds, stereoisomers or pharmaceutically acceptable salts defined in the preceding paragraphs; and a pharmaceutically acceptable excipient.

A further aspect of the invention provides a compound of Formula 1, a stereoisomer thereof or a pharmaceutically acceptable salt of the compound or stereoisomer, or any one of the compounds, stereoisomers or pharmaceutically acceptable salts defined in the preceding paragraphs, for use as a medicament.

An additional aspect of the invention provides a compound of Formula 1, a stereoisomer thereof or a pharmaceutically acceptable salt of the compound or stereoisomer, or any one of the compounds, stereoisomers or pharmaceutically acceptable salts defined in the preceding paragraphs, for treatment of a disease, disorder or condition selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, atherosclerosis, and Prader-Willi syndrome.

Another aspect of the invention provides a use of a compound of Formula 1, a stereoisomer thereof or a pharmaceutically acceptable salt of the compound or stereoisomer, or any one of the compounds, stereoisomers or pharmaceutically acceptable salts defined in the preceding paragraphs, for the manufacture of a medicament for the treatment of a disease, disorder or condition associated with MetAP2.

A further aspect of the invention provides a method of treating a disease, disorder or condition associated with MetAP2, the method comprising administering to the subject an effective amount of a compound of Formula 1, a stereoisomer thereof or a pharmaceutically acceptable salt of the compound or stereoisomer, or any one of the compounds, stereoisomers or pharmaceutically acceptable salts defined in the preceding paragraphs.

An additional aspect of the invention provides a method of treating a disease, disorder or condition in a subject, the method comprising administering to the subject an effective amount of a compound of Formula 1, a stereoisomer thereof or a pharmaceutically acceptable salt of the compound or stereoisomer, or any one of the compounds, stereoisomers or pharmaceutically acceptable salts defined in the preceding paragraphs, wherein the disease, disorder or condition is selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, atherosclerosis, and Prader-Willi syndrome.

Another aspect of the invention provides an effective amount of a compound of Formula 1, a stereoisomer thereof or a pharmaceutically acceptable salt of the compound or stereoisomer, or any one of the compounds, stereoisomers or pharmaceutically acceptable salts defined in the preceding paragraphs; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with MetAP2" and similar phrases relate to a disease, disorder or condition in a subject for which inhibition of MetAP2 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIPEA (N,N-diisopropylethylamine, Hunig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (effective concentration at half maximal response); EDA ethoxylated dodecyl alcohol, Brij® 35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate (V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); OTf (triflate); PE (petroleumether); Ph (phenyl); $pIC_{50}$ ($-\log_{10}$ ($IC_{50}$), where $IC_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating obesity and other diseases, disorders or conditions associated with MetAP2.

In addition to the specific compounds in the examples, compounds of Formula 1 include those in which (i) $R^1$ and $R^2$ are each independently selected from phenyl and $C_{3-5}$ heteroaryl, and each phenyl and $C_{3-5}$ heteroaryl is independently substituted with from 0 to 3 $R^a$; (ii) each $R^1$ and $R^2$ is independently selected from phenyl and $C_{3-5}$ heteroaryl, each $C_{3-5}$ heteroaryl having 5 ring atoms, wherein each phenyl and $C_{3-5}$ heteroaryl is independently substituted with from 0 to 3 $R^a$; (iii) each $R^1$ and $R^2$ is independently selected from phenyl and $C_{3-5}$ heteroaryl, each $C_{3-5}$ heteroaryl having 6 ring atoms, wherein each phenyl and $C_{3-5}$ heteroaryl is independently substituted with from 0 to 3 $R^a$; or (iv) each $R^1$ and $R^2$ is independently selected from phenyl and $C_{3-5}$ heteroaryl, each $C_{3-5}$ heteroaryl is pyridinyl, and each phenyl and $C_{3-5}$ heteroaryl is independently substituted with from 0 to 3 $R^a$.

Compounds of Formula 1 also include those in which (v) each $R^1$ and $R^2$ is independently selected from phenyl and $C_{3-5}$ heteroaryl, and each $C_{3-5}$ heteroaryl is independently selected from pyrrolyl, furanyl, thienyl, pyrazolyl, imidazolyl, isoxazolyl, oxazolyl, isothiazolyl, thiazolyl, pyridinyl, pyridazinyl, pyrimidinyl, and pyrazinyl, wherein each phenyl and $C_{3-5}$ heteroaryl is independently substituted with from 0 to 3 $R^a$.

In addition, or as an alternative, to one of embodiments (i) through (v) in the preceding paragraphs, compounds of Formula 1 include those in which (vi) $R^1$ and $R^2$ are both $C_{3-5}$ heteroaryl, and each $C_{3-5}$ heteroaryl is independently substituted with from 0 to 3 $R^a$.

Compounds of Formula 1 also include those in which (vii) $R^1$ and $R^2$ are both phenyl, and each phenyl is independently substituted with from 0 to 3 $R^a$.

In addition, or as an alternative, to one of embodiments (i) through (vii) in the preceding paragraphs, compounds of Formula 1 include those in which (viii):
each $R^a$ is independently selected from halo, —CN, $R^3$, and $R^4$;
each $R^3$ is independently selected from —OR$^4$, —N(R$^4$)R$^5$, —NR$^4$C(O)R$^6$, and —C(O)N(R$^4$)R$^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, which is substituted with from 0 to 3 $R^c$;
each $R^6$ is independently selected from
  (a) $C_{1-6}$ alkyl, which is substituted with from 0 to 3 $R^b$, and
  (b) $C_{6-14}$ aryl-(CH$_2$)$_m$—, which is substituted with from 0 to 3 $R^c$;
each $R^b$ is independently selected from halo, —CN, and $R^7$;
each $R^c$ and $R^d$ is independently selected from
  (a) halo, —CN, and $R^7$, and
  (b) $C_{1-6}$ alkyl, which is substituted with from 0 to 3 $R^b$;
each $R^7$ is independently selected from —OR$^8$, —N(R$^8$)R$^9$, —NR$^8$C(O)R$^9$, and —C(O)N(R$^8$)R$^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and —CN.

In addition, or as an alternative, to one of embodiments (i) through (vii) in the preceding paragraphs, compounds of Formula 1 include those in which (ix):
each $R^a$ is independently selected from halo, —CN, $R^3$, and $R^4$;
each $R^3$ is independently selected from —OR$^4$ and —N(R$^4$)R$^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, wherein the $C_{6-14}$ aryl moiety is phenyl substituted with from 0 to 3 substituents independently selected from $R^b$ and $C_{1-6}$ alkyl, and each $C_{1-6}$ alkyl is independently substituted with from 0 to 3 $R^b$;
each $R^b$ is independently selected from halo, —CN, and $R^7$;
each $R^c$ is independently selected from
  (a) halo, —CN, and $R^7$, and
  (b) $C_{1-6}$ alkyl, which is substituted with from 0 to 3 $R^b$;
each $R^7$ is independently selected from —OR$^8$ and —N(R$^8$)R$^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and —CN.

In addition, or as an alternative, to one of embodiments (i) through (vii) in the preceding paragraphs, compounds of Formula 1 include those in which (x):
each $R^a$ is independently selected from halo, —CN, $R^3$, and $R^4$;
each $R^3$ is independently selected from —OR$^4$ and —N(R$^4$)R$^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, wherein the $C_{6-14}$ aryl moiety is phenyl substituted with from 0 to 3 substituents independently selected from $R^b$ and $C_{1-6}$ alkyl, and each $C_{1-6}$ alkyl is independently substituted with from 0 to 3 $R^b$;
each $R^b$ is independently selected from halo and —CN; and
each $R^c$ is independently selected from halo, —CN, and $C_{1-6}$ alkyl substituted with from 0 to 3 $R^b$.

In addition, or as an alternative, to one of embodiments (i) through (vii) in the preceding paragraphs, compounds of Formula 1 include those in which (xi):
each $R^a$ is independently selected from halo, —CN, $R^3$, and $R^4$;
each $R^3$ is independently selected from —OR$^4$ and —N(R$^4$)R$^5$;
each $R^4$ and $R^5$ is independently selected from $C_{1-6}$ alkyl substituted with from 0 to 3 $R^b$; and
each $R^b$ is independently selected from halo and —CN.

In addition, or as an alternative, to one of embodiments (i) through (vii) in the preceding paragraphs, compounds of Formula 1 include those in which (xii) $R^a$ is absent.

Compounds of Formula 1 also include those in which (xiii) $R^1$ and $R^2$ are each independently —OR$^4$ or —N(R$^4$)R$^5$; (xiv) $R^1$ and $R^2$ are both —OR$^4$; or (xv) $R^1$ and $R^2$ are both —N(R$^4$)R$^5$.

In addition, or as an alternative, to one of embodiments (xiii) through (xv) in the preceding paragraph, compounds of Formula 1 include those in which (xvi):

each $R^4$ and $R^5$ is independently selected from
(a) $C_{1-6}$ alkyl, which is substituted with from 0 to 3 $R^b$, and
(b) $C_{6-14}$ aryl-$(CH_2)_m$—, which is substituted with from 0 to 3 $R^c$;
each $R^b$ is independently selected from halo, —CN, and $R^7$;
each $R^c$ is independently selected from
(a) halo, —CN, and $R^7$, and
(b) $C_{1-6}$ alkyl substituted with from 0 to 3 $R^b$;
each $R^7$ is independently selected from —$OR^8$, —$N(R^8)R^9$, —$NR^8C(O)R^9$, and —$C(O)N(R^8)R^9$; and
each $R^8$ and $R^9$ is independently selected from $C_{1-6}$ alkyl and $C_{3-8}$ cycloalkyl-$(CH_2)_m$—, each substituted with from 0 to 3 substituents independently selected from halo and —CN.

In addition, or as an alternative, to one of embodiments (xiii) through (xv) in a preceding paragraph, compounds of Formula 1 include those in which (xvii):
each $R^4$ and $R^5$ is independently selected from
(a) $C_{1-6}$ alkyl substituted with from 0 to 3 $R^b$, and
(b) $C_{6-14}$ aryl-$(CH_2)_m$—, wherein the $C_{6-14}$ aryl moiety is phenyl substituted with from 0 to 3 $R^c$;
each $R^b$ is independently selected from halo, —CN, and $R^7$;
each $R^c$ is independently selected from
(a) halo, —CN, and $R^7$, and
(b) $C_{1-6}$ alkyl substituted with from 0 to 3 $R^b$;
each $R^7$ is independently selected from —$OR^8$ and —$N(R^8)R^9$; and
each $R^8$ and $R^9$ is independently selected from $C_{1-6}$ alkyl and $C_{3-8}$ cycloalkyl-$(CH_2)_m$—, each substituted with from 0 to 3 substituents independently selected from halo and —CN.

In addition, or as an alternative, to one of embodiments (xiii) through (xv) in a preceding paragraph, compounds of Formula 1 include those in which (xviii):
each $R^4$ and $R^5$ is independently selected from
(a) $C_{1-6}$ alkyl, which is substituted with from 0 to 3 $R^b$, and
(b) $C_{6-14}$ aryl-$(CH_2)_m$—, wherein the $C_{6-14}$ aryl moiety is phenyl substituted with from 0 to 3 $R^c$;
each $R^b$ is independently selected from halo and —CN; and
each $R^c$ is independently selected from halo, —CN, and $C_{1-6}$ alkyl, which is substituted with from 0 to 3 $R^b$.

In addition, or as an alternative, to one of embodiments (xiii) through (xv) in a preceding paragraph, compounds of Formula 1 include those in which (xix):
each $R^4$ and $R^5$ is independently selected from $C_{1-6}$ alkyl substituted with from 0 to 3 $R^b$; and
each $R^b$ is independently selected from halo and —CN.

In addition, or as an alternative, to one of embodiments (xiii) through (xv) in a preceding paragraph, compounds of Formula 1 include those in which (xx):
each $R^4$ and $R^5$ is independently selected from $C_{1-3}$ alkyl substituted with from 0 to 3 $R^b$; and
each $R^b$ is independently selected from halo and —CN.

In addition, or as an alternative, to one of embodiments (xiii) through (xv) in a preceding paragraph, compounds of Formula 1 include those in which (xxi):
each $R^4$ and $R^5$ is independently selected from methyl and ethyl, each substituted with from 0 to 3 $R^b$; and
each $R^b$ is independently selected from halo and —CN.

In addition, or as an alternative, to one of embodiments (xiii) through (xv) in a preceding paragraph, compounds of Formula 1 include those in which (xxii):
each $R^4$ and $R^5$ is independently methyl substituted with from 0 to 3 $R^b$; and
each $R^b$ is independently selected from halo and —CN.

In addition, or as an alternative, to one of embodiments (xiii) through (xv) in a preceding paragraph, compounds of Formula 1 include those in which (xxiii):
each $R^4$ and $R^5$ is independently ethyl substituted with from 0 to 3 $R^b$; and
each $R^b$ is independently selected from halo and —CN.

In addition, or as an alternative, to one of embodiments (i) to (viii) in the preceding paragraphs, compounds of Formula 1 include those in which (xxiv) $R^d$ is absent.

In addition, or as an alternative, to one of embodiments (i) to (x), (xiii) to (xviii), and (xxiv) in the preceding paragraphs, compounds of Formula 1 include those in which (xxv) m is 0, 1, 2 or 3; (xxvi) m is 0, 1 or 2; (xxvii) m is 0 or 1; or (xxviii) m is 0.

In addition, or as an alternative, to one of embodiments (i) to (x), (xiii) to (xviii), and (xxiv) to (xxviii) in the preceding paragraphs, compounds of Formula 1 include those in which (xxix) $R^c$ is absent.

In addition, or as an alternative, to one of embodiments (i) to (xxix) in the preceding paragraphs, compounds of Formula 1 include those in which (xxx) $R^b$ is absent.

Compounds of Formula 1 include embodiments (i) through (xxx) described in the preceding paragraphs and all compounds specifically named above and in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-$ $Na^+$, —$COO^-K^+$, —$SO_3^-Na^+$) or polar non-ionic moiety (such as —$N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the scheme, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^2$ substituent having a potentially reactive amine. In such cases, $R^2$ would include the moiety with or without, say, a Boc or Cbz group attached to the amine.

Scheme A shows a general method for preparing compounds of Formula 1. According to the method, fumagillol (A1) is reacted with a vinyl phosphine oxide (A2 in which $R^1$ and $R^2$ are independently phenyl or $C_{3-5}$ heteroaryl, each optionally substituted with 1-3 $R^a$), a P-vinyl phosphinate or P-vinyl phosphinic amide (A2 in which one of $R^1$ and $R^2$ is phenyl or $C_{3-5}$ heteroaryl, each optionally substituted, and the other is —OR$^4$ or —N(R$^4$)R$^5$, respectively), a P-vinyl phosphonate or vinyl phosphonic diamide (A2 in which $R^1$ and $R^2$ are both —OR$^4$ or —N(R$^4$)R$^5$, respectively), or a P-vinyl phosphonamidate (A2 in which one of $R^1$ and $R^2$ is —$OR^4$ and the other is —$N(R^4)R^5$). The oxa-Michael addition is carried out in the presence of a strong base (e.g., KOH, NaOH, LiOH, NaH, etc.) and in one or more compatible solvents (DMF, toluene, methylcyclohexane, etc.), typically at room temperature. Fumagillol (A1) may be prepared by base hydrolysis of fumagillin. For example, fumagillin, which is commercially available as a dicyclohexylamine salt, may be contacted with aqueous sodium hydroxide at room temperature to give A1. The vinyl reactant (A2) may be prepared using methods known in the art, for example, by reacting an appropriately substituted phosphinic chloride, phosphonochloridate, phosphonamidic chloride, phosphorochloridate, phosphorodiamidic chloride, or phosphoramidochloridate with a Grignard reagent (e.g., $CH_2$=CHMgBr) in a compatible solvent (e.g., $Et_2O$, THF) to give A2.

Scheme A

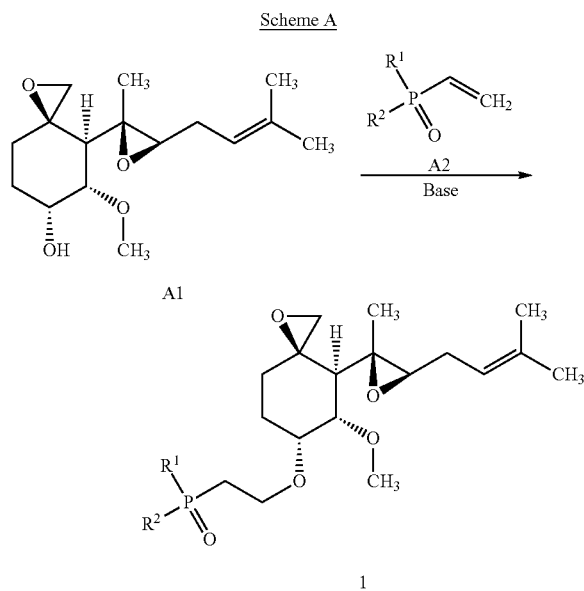

Scheme B shows another method for preparing the vinyl reactant (A2) in Scheme A. In accordance with the method, a vinyl halide or triflate (B2 in which X=Br, I, OTf) is reacted with a requisite phosphine oxide (B1 in which $R^1$ and $R^2$ are independently phenyl or $C_{3-5}$ heteroaryl, each optionally substituted), a phosphinate or phosphinic amide (B1 in which one of $R^1$ and $R^2$ is phenyl or $C_{3-5}$ heteroaryl, each optionally substituted, and the other is —$OR^4$ or —$N(R^4)R^5$), a phosphonate or phosphonic diamide (B1 in which $R^1$ and $R^2$ are both —$OR^4$ or —$N(R^4)R^5$), or a phosphonamidate (B1 in which one of $R^1$ and $R^2$ is —$OR^4$ and the other is —$N(R^4)R^5$). The reaction occurs in the presence of a palladium catalyst (e.g., $Pd(PPh_3)_4$) and base ($Et_3N$, $Na_2CO_3$, $K_2CO_3$, $Cs_2CO_3$, $K_3PO_4$, etc.) in a compatible solvent (THF, DMF, dioxane, toluene, etc.), typically at elevated temperature. See, e.g. Xu et al., *Synthesis* 8:691-92 (1986) (reacting diphenylphosphine oxide and vinyl bromide with $Pd(Ph_3P)_4$ and $Et_3N$ in toluene at 60° C. for 8 hours yields diphenyl(vinyl)phosphine oxide); see also Kalek et al., *Organic Letters* 10(20):4637-40 (2008) (reacting diethyl phosphonate and vinyl bromide with $Pd(Ph_3P)_4$ and $Cs_2CO_3$ in THF at 120° C. for 10 minutes in a microwave reactor yields diethyl vinylphosphonate).

Scheme B

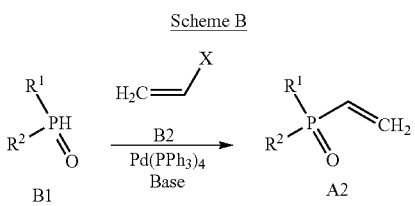

The methods depicted in the schemes may be varied as desired. For example, protecting groups may be added or removed and products may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, antifoaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinyl alcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which inhibition of MetAP2 is indicated. Such diseases, disorders, and conditions generally relate to any unhealthy or abnormal state in a subject for which the inhibition of MetAP2 provides a therapeutic benefit. More particularly, the compounds of Formula 1 may be used to treat obesity or an overweight condition in a subject, or to treat diseases, disorders or conditions associated with obesity or an overweight condition, including cardiovascular disease, hypertension, diabetes, hyperglycemia, insulin resistance, metabolic syndrome X, impaired glucose tolerance, non-alcoholic liver steatosis, dyslipidemia (including high total cholesterol or high levels of triglycerides), atherosclerosis, stroke, sleep apnea, osteoarthritis, infertility, polycystic ovary syndrome, and Prader-Willi syndrome.

According to *The Practical Guide: Identification, Evaluation, and Treatment of Overweight and Obesity in Adults*, published in 2000 by the National Heart, Lung, and Blood Institute, a human adult may be classified as overweight or obese based upon the subject's body mass index (BMI). BMI is calculated by dividing a subject's mass (in kg) by the square of the subject's height (in meters). Under the Guide, a BMI of 25-29.9 kg/m$^2$ is classified as overweight, and body mass indices of 30-34.9 kg/m$^2$, 35-39.9 kg/m$^2$, and ≥40 kg/m$^2$ are classified as Class 1 obesity, Class 2 obesity, and Class 3 (extreme) obesity, respectively.

The claimed and disclosed compounds may be combined with one or more other pharmacologically active compounds or therapies to treat one or more disorders, diseases or conditions for which MetAP2 is indicated, including obesity. For example, compounds of Formula 1, which include compounds specifically named above, and their pharmaceutically acceptable complexes, salts, solvates and hydrates, may be administered simultaneously, sequentially or separately in combination with one or more compounds or therapies for treating cardiovascular disease, hypertension, diabetes, hyperglycemia, insulin resistance, metabolic syndrome X, impaired glucose tolerance, non-alcoholic liver steatosis, dyslipidemia, atherosclerosis, stroke, sleep apnea, osteoarthritis, infertility, polycystic ovary syndrome, and Prader-Willi syndrome. Such combinations may offer significant therapeutic advantages, including fewer side effects, improved ability to treat underserved patient populations, or synergistic activity.

For example, the compounds of Formula 1 may be combined with one or more agents for treating obesity, diabetes, hyperglycemia, insulin resistance, metabolic syndrome X, impaired glucose tolerance, and non-alcoholic liver steatosis. These agents include pancreatic lipase inhibitors (e.g., orlistat); insulin; insulin sensitizers, including biguanides (e.g., buformin, metformin, and phenformin) and glitazones (e.g., pioglitazone and rosiglitazone); insulin secretagogues, including sulfonylureas (e.g., acetohexamide, chlorpropamide, tolazamide, tolbutamide, gliclazide, glimepiride, glipizide, and glyburide), and meglitinides (e.g., nateglinide and repaglinide); alpha-glucosidase inhibitors (e.g., acarbose and miglitol); glucagon-like peptide analogs and agonists (e.g., exenatide, liraglutide, and taspoglutide); dipeptidyl peptidase-4 inhibitors (e.g., alogliptin, linagliptin, saxagliptin, sitagliptin, and vildagliptin); and amylin analogs (e.g., pramlinitide).

In addition, the compounds of Formula 1 may be combined with one or more agents for treating osteoarthritis, including nonsteroidal anti-inflamatory drugs (NSAIDs) (e.g., apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac); analgesics (e.g., acetaminophen and morphine sulfate, as well as codeine, hydrocodone, oxycodone, propoxyphene, and tramadol, all with or without acetaminophen); corticosteroids (e.g., betamethasone, cortisone acetate, dexamethasone, hydrocortisone, methylprednisolone, prednisolone, and prednisone); and osteoporosis agents (e.g., alendronate, clodronate, etidronate, ibandronate, neridronate, olpadronate, pamidronate, risedronate, tiludronate, and zoledronate).

The compounds of Formula 1 may also be combined with one or more agents for treating cardiovascular disease, hypertension, dyslipidemia, atherosclerosis, and stroke, including calcium channel blockers (e.g., amlodipine, aranidipine, azelnidipine, barnidipine, bepridil, benidipine, cilnidipine, clevidipine, diltiazem, isradipine, efonidipine, felodipine, fendiline, fluspirilene, lacidipine, lercanidipine, manidipine, mibefradil, nicardipine, nifedipine, nilvadipine, nimodipine, nisoldipine, nitrendipine, pranidipine, and verapamil); statins (e.g., atorvastatin, fluvastatin, lovastatin, mevastatin, pitavastatin, pravastatin, rosuvastatin, and simvastatin); PPAR alpha activators (e.g., fibrates, such as bezafibrate, ciprofibrate, clofibrate, fenofibrate, and gemfibrozil); bile acid sequestrants (e.g., cholestyramine, colesevelam, and colestipol); other lipid-lowering agents (e.g., niacin and ezetimibe); beta-blockers (e.g., alprenolol, atenolol, betaxolol, bisoprolol, bucindolol, carteolol, carvedilol, celiprolol, esmolol, eucommia bark, labetalol, metoprolol, nadolol, nebivolol, oxprenolol, penbutolol, pindolol, propranolol, sotalol, and timolol); angeotensin-converting enzyme (ACE) inhibitors (benazepril, captopril, enalapril, imidapril, lisinopril, perindopril, quinapril, ramipril, trandolapril, and zofenopril); and platelet aggregation inhibitors (abciximab, aspirin, cilostazol, clopidogrel, dipyridamole, dipyridamole, eptifibatide, ifetroban, picotamide, prasugrel, terutroban, ticagrelor, ticlopidine, and tirofiban).

Biological Activity

The biological activity of the compound of Formula 1 may be determined using various in vitro and in vivo methods. The following in vitro assays measure a test compound's ability to inhibit MetAP2. The in vivo assays measure a test compound's ability to induce body weight loss or hypoglycemic activity.

MetAP2 Protein Purification

DNA encoding the full-length sequence of human MetAP2 enzyme is amplified by PCR and cloned into a pFastBac expression vector (Invitrogen). Recombinant baculovirus incorporating the MetAP2 construct is generated by transposition using the Bac-to-Bac system (Invitrogen). The expression of recombinant protein is carried out by infection of Spodoptera frugiperda Sf9 cells (Invitrogen) in 5 L Wave Bioreactors (Wave Biotech). Recombinant protein is isolated from cellular extracts by binding to an SP Hitrap Fast Flow or SP Sepharose (Sigma) column, and the protein is eluted using a NaCl gradient. Partially purified extracts of MetAP2 are further purified by an AKTA FPLC over a Superdex-200 column (GE). The purity of MetAP2 protein is determined on denaturing SDS-PAGE gel. Purified MetAP2 protein is concentrated to a final concentration of 17 mg/mL or 2.5 mg/mL. The protein is stored at −78° C. in a buffer containing 10 mM HEPES pH 7.4, 150 mM NaCl, and 1 mM $CoCl_2$ or in a buffer containing 20 mM HEPES pH 7.4, 120 mM NaCl, and 5 mM $MnCl_2$.

Enzyme Assay: Inhibition of MetAP2

The inhibition of MetAP2 is determined using a black 384-well-plate format under the following reaction conditions: 50 mM Hepes pH 7.5, 100 mM NaCl, 10 μM $MnCl_2$ or 10 μM $CoCl_2$, 0.005% Brij35®, 1 mM TCEP, 1% DMSO. To initiate the assay, 4 μL of 5 to 50 nM MetAP2 enzyme solution (enzyme final concentration is 2 to 20 nM) is added to each well, followed by the addition of 2 μL of the test compound (2.5-fold serial dilutions for 11 data points for each test compound) in a buffer solution containing 5% DMSO. Next, 4 μL of a substrate solution (2.5×$K_m$ of Met-AMC) is added to each well of the plate (final substrate concentration at $K_m$ value). The reaction rate is monitored by reading fluorescence at 460 nm with excitation wavelength at 330 nm for 10 to 30 minutes using a fluorescence plate reader. The results for each well are expressed as percent inhibition and calculated using the equation:

$$\text{Inhibition} = 1 - \left( \frac{x - \overline{\text{Positive}}}{\overline{\text{Negative}} - \overline{\text{Positive}}} \right),$$

where $\overline{\text{Negative}}$ is the average of all the rates on the plate in the presence of no test compound, $\overline{\text{Positive}}$ is the rate with a 10 μM tool compound (MetAP2 activity is 100% inhibited), and x is the rate (raw data) in the presence of the test compound. The $IC_{50}$ for each test compound is obtained by fitting the percent inhibition data with a standard 4-parameter equation and is reported as $pIC_{50}$, i.e., $-\log(IC_{50})$, where $IC_{50}$ is the molar concentration at 50% inhibition.

MetAP2 Cellular Activity: Western Blotting of NMet-14-3-3γ

HUVEC cells (Lonza) are seeded in 96-well tissue culture microplates and cultured for 24 hours prior to addition of test compounds (11 point range of serial dilutions) or DMSO vehicle. After 24 hours, whole cell extracts are prepared by lysing cells in cell extraction buffer (Cell Signaling) containing protease and phosphatase inhibitors (Calbiochem). Insoluble material is removed by centrifugation and samples are diluted and boiled in SDS-PAGE buffer. Proteins are resolved by SDS-PAGE and transferred to PVDF membranes. Membranes are blocked then incubated with the appropriate primary antibodies, NMet-14-3-3γ (Novus) and β-actin (Sigma), followed by incubation with secondary IRDye 680- or 800CW-conjugated antibodies (Li-Cor). Membranes are scanned on the Odyssey (Li-Cor) and signals corresponding to N-Met14-3-3γ and β-actin are quantified using LiCor software. Compound $EC_{50}$s are obtained by curve-fitting the ratios of unprocessed N-Met14-3-3γ protein signal over γ-actin protein signal using XLfit4 Microsoft Excel curve-fitting software and are reported as $pEC_{50}$, i.e., $-\log(EC_{50})$, where $EC_{50}$ is the molar concentration at 50% effective (maximal) response.

Body Weight Loss

Ten to twelve weeks old male C57bl/6 mice are obtained from commercial vendors, and placed on high-fat diet (60% kcal fat) for at least 15 weeks. Treatment with MetAP2 inhibitors is initiated when the average body weight reaches approximately 50 g. The MetAP2 inhibitors are formulated in an aqueous solution of 0.5% methyl cellulose and administered through oral gavage. Control animals receive the equivalent volume of aqueous 0.5% methyl cellulose solution without a MetAP2 inhibitor. Body weight (BW) and food intake are recorded daily, and efficacy is calculated individually as a percentage of BW loss relative to the pretreatment values. Depending on the study design, the treatment is continued for 12, 14 or 28 days. In some studies, indirect calorimetry or body composition are determined at the end of the treatment.

Hypoglycemic Activity

Six-week-old male $KKA^y$ mice are obtained from commercial vendors and placed on standard chow. Treatment with a MetAP2 inhibitor is initiated after 8-day acclimization. The MetAP2 inhibitor is formulated in an aqueous 0.5% methylcellulose solution, which is administered once daily through oral gavage. Control animals are treated with the equivalent volume of aqueous 0.5% methylcellulose solution without the compound. After 4 weeks, blood is collected from the tail vein of each of the mice. Glycated hemoglobin levels are measured using a Tosoh HLC-723G8 automated glycohemoglobin analyzer, and plasma glucose levels are measured using a Hitachi model 7180 automated glucose analyzer. For evaluation of the hypoglycemic activity of the MetAP2 inhibitor, statistical differences between control- and compound-treated groups are analyzed using a one-tailed Williams test.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for [M+H]$^+$) were recorded using either electrospray ionization (ESI-MS) or atmospheric pressure chemical ionization (APCI-MS) mass spectrometry.

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5μ C18 110 A, Axia™, 30×75 mm, 5μ) under acidic conditions ("acid mode") eluting with $CH_3CN$ and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., Gene-Vac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation 1: (3R,4S,5S,6R)-5-methoxy-4-((2R,3R)-2-methyl-3-(3-methylbut-2-en-1-yl)oxiran-2-yl)-1-oxaspiro[2.5]octan-6-ol

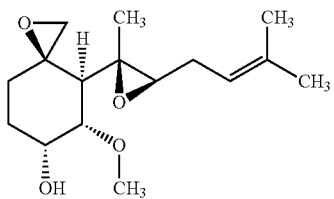 [SMILES: CO[C@@H]1[C@H](O)CC[C@]2(CO2)[C@H]1[C@@]1(C)O[C@@H]1CC=C(C)C]

A 1-L 3-neck round bottom flask was charged with 1.5 M NaOH aq (263 mL, 395 mmol) followed by dicyclohexylamine (2E,4E,6E,8E)-10-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)-10-oxodeca-2,4,6,8-tetraenoate (79 g, 123 mmol). The resulting mixture was stirred at room temperature overnight during which a brown solid precipitate was formed. TLC showed the title compound was the major product. Ethyl acetate (200 mL) was added and the mixture was stirred at room temperature for 10 minutes. A yellow precipitate formed during the addition and the aggregated solid broke into smaller particles. Sodium chloride (35.6 g, 609 mmol) was added and the mixture was stirred for another 10 minutes. The mixture was filtered and the filter cake was washed with EtOAc (160 mL). The organic and aqueous layers were separated and the aqueous layer was extracted with EtOAc (2×200 mL). The organic layers were combined and then washed with water (96 mL), 0.4 N $H_2SO_4$ (with ammonium sulfate, 13 g/L) (2×200 mL), and brine (160 mL). The organic phase was dried over $Na_2SO_4$, filtered, and concentrated using a rotary evaporator. The residue was diluted with acetone (2×40 mL) and condensed to dryness in a rotary evaporator, yielding crude product as a light orange syrup. The residue was subsequently diluted with acetone (4.0 mL) and 3% $NaHCO_3$ aq (72 mL) and then cooled in an ice bath. The mixture was seeded with product from a previous batch and stirred for 2 hours in an ice bath. The mixture was filtered and the filter cake was washed with ice water (100 mL). The cake was air dried for 4 hours and then dried under high vacuum at room temperature overnight to give the title compound as an off-white solid (21.8 g, 62.5%). $[M+H]^+$ calc'd for $C_{16}H_{27}O_4$, 283.19; found 283.3.

Preparation 2: diphenyl(vinyl)phosphine oxide

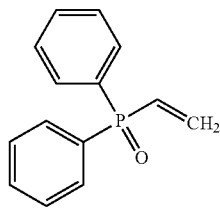 [SMILES: C=CP(=O)(c1ccccc1)c1ccccc1]

In a 500 mL 3-neck round-bottom flask equipped with a magnetic stir bar, diphenylphosphine oxide (19.2 g, 95 mmol), bromoethene (1M THF) (86 mL, 86 mmol), $Et_3N$ (39.7 mL, 285 mmol) and $Pd(Ph_3P)_4$ (4.99 g, 4.32 mmol) were mixed in toluene (150 mL) to give a yellow suspension. The mixture was purged with nitrogen and heated to 60° C. for 24 hours under $N_2$. The mixture was then cooled and filtered. The filtrate was concentrated and purified by flash chromatography (240 g column) eluting with 50-100% EtOAc in heptanes. The pure fractions were combined and concentrated to give the title compound as a light yellow solid (10 g, 51%). $[M+H]^+$ calc'd for $C_{14}H_{14}OP$, 229.08; found 229.1.

Preparation 3: di-p-tolyl(vinyl)phosphine oxide

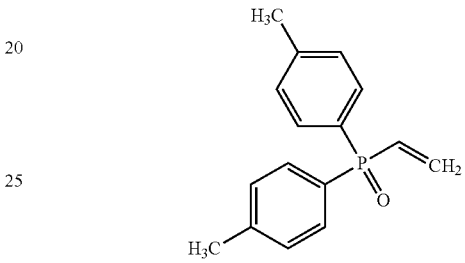

In a 40 mL vial equipped with a magnetic stir bar, di-p-tolylphosphine oxide (930 mg, 4.04 mmol), bromoethene (1M THF) (3.67 mL, 3.67 mmol), $Et_3N$ (1.689 mL, 12.12 mmol) and $Pd(Ph_3P)_4$ (424 mg, 0.367 mmol) were mixed in toluene (10 mL) to give a yellow suspension. The mixture was purged with $N_2$, the vial sealed and heated to 60° C. for 18 hours. The mixture was then cooled and filtered. The filtrate was concentrated and purified by flash chromatography (25 g column) eluting with 50-100% EtOAc in heptanes. The pure fractions were combined and concentrated to give the title compound as a clear syrup (400 mg, 42.5%). $[M+H]^+$ calc'd for $C_{16}H_{18}OP$, 257.11, found 257.1.

Preparation 4: bis(4-(trifluoromethyl)phenyl)(vinyl)phosphine oxide

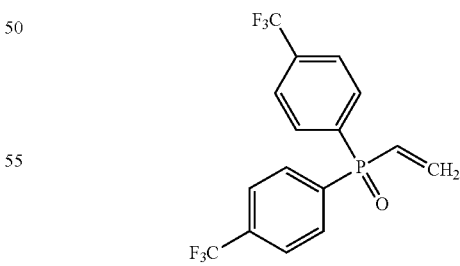

In a 40 mL vial equipped with a magnetic stir bar, bis(4-(trifluoromethyl)phenyl)phosphine oxide (930 mg, 2.75 mmol), bromoethene (1M THF) (2.500 mL, 2.500 mmol), $Et_3N$ (1.150 mL, 8.25 mmol) and $Pd(Ph_3P)_4$ (289 mg, 0.250 mmol) were mixed in toluene (10 mL) to give a yellow suspension. The mixture was purged with $N_2$, the vial sealed and heated to 80° C. for 18 hours. The mixture was then cooled and filtered. The filtrate was concentrated and purified by flash chromatography (25 g column) eluting with 50-100% EtOAc in heptanes. The pure fractions were combined and concentrated to give the title compound as a brown syrup (320 mg, 35.1%). [M+H]+ calc'd for $C_{16}H_{12}F_6OP$, 365.05, found 365.1.

Example 1: (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)diphenylphosphine oxide

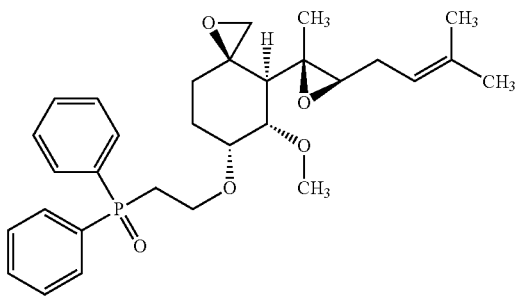 [SMILES: CO[C@@H]1[C@H](OCCP(=O)(c2ccccc2)c2ccccc2)CC[C@]2(CO2)[C@H]1[C@@]1(C)O[C@@H]1CC=C(C)C]

In an 8 mL vial equipped with a magnetic stir bar, (3R,4S,5S,6R)-5-methoxy-4-((2R,3R)-2-methyl-3-(3-methylbut-2-en-1-yl)oxiran-2-yl)-1-oxaspiro[2.5]octan-6-ol (250 mg, 0.885 mmol), diphenyl(vinyl)phosphine oxide (202 mg, 0.885 mmol), and KOH (24.84 mg, 0.443 mmol) were mixed in toluene (3 mL) to give a tan solution. The mixture was left to stir for 1.5 hours at room temperature and then filtered and concentrated. A small amount of Et$_2$O (~1.5 mL) was added to the concentrated mixture, which was swirled until it was a brown solution. The solution was seeded with product crystals from a previous batch. Crystals began to form after about a minute. The vial was capped and was allowed to sit at room temperature overnight. In the morning residual Et$_2$O was pipetted off into a separate vial and the crystals were rinsed with Et$_2$O (2×). The Et$_2$O in the separate vial showed crystal formation and was added back to the parent vial, swirled with some additional Et$_2$O, and the clear-yellow Et$_2$O solution was pipetted off. The remaining crystals were dried under a stream of N$_2$. Water (~8 mL) was then added to the vial, and the mixture was swirled and filtered. The solids were washed multiple times with water to remove any residual KOH. The resulting crystals were washed with a small amount of Et$_2$O and allowed to dry. The crystals were transferred to a vial and dried under vacuum to yield the title compound as a tan solid (320 mg, 70.8%). $^1$H NMR (400 MHz, CD$_3$OD) δ ppm 0.66-0.74 (m, 1H), 1.13 (s, 3H), 1.41-1.55 (m, 1H), 1.59-1.70 (m, 5H), 1.77 (s, 4H), 2.15-2.25 (m, 1H), 2.25-2.36 (m, 1H), 2.40 (d, J=4.29 Hz, 1H), 2.44-2.51 (m, 1H), 2.69 (ddt, 1H), 2.83 (d, J=4.29 Hz, 1H), 2.93 (dtd, J=15.32, 8.38, 8.38, 6.82 Hz, 1H), 3.32-3.42 (m, 3H), 3.42-3.50 (m, 1H), 3.83-4.03 (m, 3H), 5.21-5.27 (m, 1H), 7.49-7.60 (m, 6H), 7.72-7.86 (m, 4H). [M+H]+ calc'd for $C_{30}H_{40}O_5P$, 511.26; found 511.4.

Example 2: (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)di-p-tolylphosphine oxide

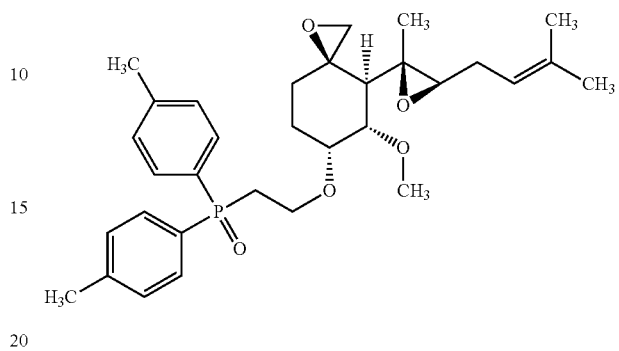

In a 50 mL round-bottomed flask equipped with a magnetic stir bar, (3R,4S,5S,6R)-5-methoxy-4-((2R,3R)-2-methyl-3-(3-methylbut-2-en-1-yl)oxiran-2-yl)-1-oxaspiro[2.5]octan-6-ol (441 mg, 1.561 mmol), dip-tolyl(vinyl) phosphine oxide (400 mg, 1.561 mmol), and KOH (26.3 mg, 0.468 mmol) were mixed in toluene (3 mL) to give a colorless suspension. The mixture was left to stir for 2 hours. The product was purified by preparative HPLC, eluting with 45-85% CH$_3$CN in 10 mM aq NH$_4$HCO$_3$. The pure fractions were combined and concentrated to give the title compound as a sticky white foam (225 mg, 27%). $^1$H NMR (400 MHz, CD$_3$OD) δ ppm 0.67-0.73 (m, 1H), 1.13 (s, 3H), 1.18 (t, J=7.07 Hz, 1H), 1.43-1.53 (m, 1H), 1.58-1.67 (m, 2H), 1.69 (s, 3H), 1.77 (s, 3H), 1.79-1.85 (m, 1H), 2.17-2.25 (m, 1H), 2.29-2.36 (m, 1H), 2.36-2.42 (m, 7H), 2.42-2.47 (m, 1H), 2.58-2.68 (m, 1H), 2.82-2.85 (m, 1H), 2.85-2.91 (m, 1H), 3.37 (s, 3H), 3.46-3.49 (m, 1H), 3.49-3.52 (m, 1H), 3.79-3.89 (m, 1H), 3.93-4.02 (m, 2H), 5.22-5.28 (m, 1H), 7.31-7.36 (m, 4H), 7.58-7.65 (m, 2H), 7.65-7.72 (m, 2H). [M+H]+ calc'd for $C_{32}H_{44}O_5P$, 539.29; found 539.4.

Example 3: (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)bis(4-(trifluoromethyl)phenyl)phosphine oxide

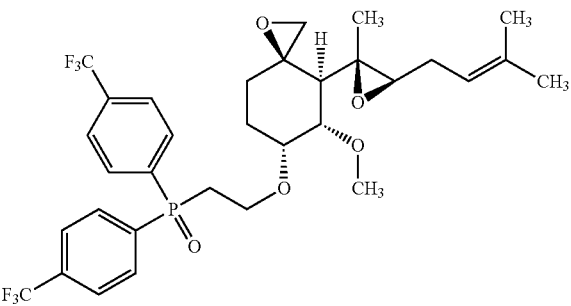 [SMILES: CO[C@@H]1[C@H](OCCP(=O)(c2ccc(C(F)(F)F)cc2)c2ccc(C(F)(F)F)cc2)CC[C@]2(CO2)[C@H]1[C@@]1(C)O[C@@H]1CC=C(C)C]

In a 20 mL round-bottom flask equipped with a magnetic stir bar, (3R,4S,5S,6R)-5-methoxy-4-((2R,3R)-2-methyl-3-(3-methylbut-2-en-1-yl)oxiran-2-yl)-1-oxaspiro[2.5]octan-6-ol (248 mg, 0.879 mmol), bis(4-(trifluoromethyl)phenyl) (vinyl)phosphine oxide (320 mg, 0.879 mmol), and KOH (14.79 mg, 0.264 mmol) were mixed in toluene (3 mL) to give a colorless suspension. The mixture was left to stir for 2 hours. The product was purified by preparative HPLC, eluting with 45-85% CH$_3$CN in 10 mM aq NH$_4$HCO$_3$. The pure fractions were combined and lyophilized to give the title compound as a white fluffy solid (127.6 mg, 22.46%). $^1$H NMR (400 MHz, CD$_3$OD) δ ppm 0.64 (d, J=13.14 Hz, 1H), 1.13 (s, 3H), 1.36 (dd, J=13.52, 4.17 Hz, 1H), 1.44-1.53 (m, 2H), 1.68 (s, 3H), 1.75-1.81 (m, 4H), 2.18 (d, J=6.82 Hz, 1H), 2.29-2.36 (m, 2H), 2.36-2.41 (m, 1H), 2.75 (s, 1H), 2.81 (d, J=4.29 Hz, 1H), 3.06-3.16 (m, 1H), 3.39 (s, 3H), 3.49 (dd, J=11.37, 2.53 Hz, 1H), 3.91-4.12 (m, 3H), 5.19-5.25 (m, 1H), 7.85 (dt, J=5.56, 2.78 Hz, 4H), 8.00 (dd, J=11.37, 8.08 Hz, 2H), 8.09 (dd, J=11.49, 7.96 Hz, 2H). [M+H]$^+$ calc'd for C$_{32}$H$_{38}$F$_6$O$_5$P, 647.24; found 647.4.

Example 4: dimethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate

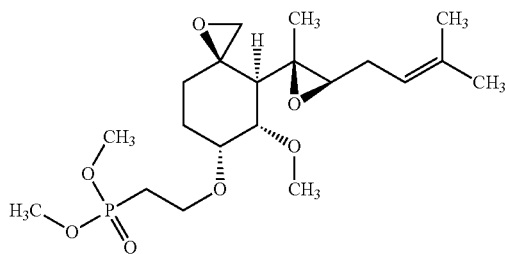 [SMILES: CO[C@@H]1[C@H](OCCP(=O)(OC)OC)CC[C@]2(CO2)[C@H]1[C@@]1(C)O[C@@H]1CC=C(C)C]

In a 20 mL vial equipped with a magnetic stir bar, (3R,4S,5S,6R)-5-methoxy-4-((2R,3R)-2-methyl-3-(3-methylbut-2-en-1-yl)oxiran-2-yl)-1-oxaspiro[2.5]octan-6-ol (835 mg, 2.96 mmol), dimethyl vinylphosphonate (523 mg, 3.84 mmol), and KOH (1161 mg, 20.70 mmol) were mixed in DMF to give a colorless suspension. The mixture was left to stir for 20 minutes at room temperature. The product was decanted away from undissolved KOH and partitioned between water (70 mL) and ethyl acetate (75 mL). The layers were separated and the aqueous layer was back-extracted with ethyl acetate (75 mL). The organic layers were combined, washed with brine (30 mL), and the organic layer was concentrated to yield a yellow syrup. The product was purified by preparative HPLC, eluting with 35-75% CH$_3$CN in 10 mM aq NH$_4$HCO$_3$. The pure fractions were combined and extracted with Et$_2$O (2×200 mL). The combined organic extracts were concentrated to yield a yellow liquid, which was dissolved in CH$_3$CN/water (1:1) and then lyophilized to give the title compound as an off-white hygroscopic solid (380 mg, 30.7%). $^1$H NMR (400 MHz, CD$_3$OD) δ ppm 0.92-0.98 (m, 1H), 1.18 (s, 3H), 1.61-1.68 (m, 4H), 1.75 (s, 3H), 1.99-2.05 (m, 2H), 2.11-2.26 (m, 4H), 2.26-2.35 (m, 1H), 2.52 (d, J=4.29 Hz, 1H), 2.60 (t, J=6.32 Hz, 1H), 2.94 (d, J=4.04 Hz, 1H), 3.36-3.45 (m, 3H), 3.48 (s, 1H), 3.59 (dd, J=11.24, 2.40 Hz, 1H), 3.74 (dd, J=10.99, 1.64 Hz, 6H), 3.77-3.84 (m, 2H), 4.11 (br s, 1H), 5.21-5.26 (m, 1H). [M+H]$^+$ calc'd for C$_{20}$H$_{36}$O$_7$P, 419.22; found 419.3.

Example 5: diethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate

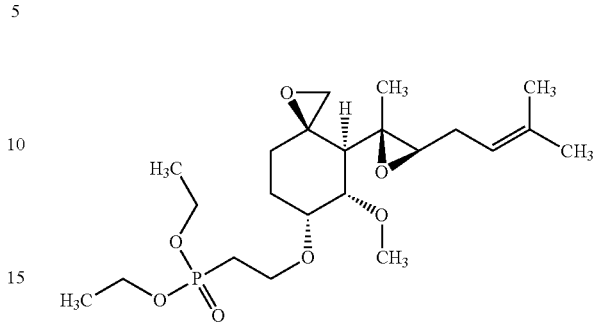

In a dry 100 mL round-bottomed flask equipped with a magnetic stir bar, (3R,4S,5S,6R)-5-methoxy-4-((2R,3R)-2-methyl-3-(3-methylbut-2-en-1-yl)oxiran-2-yl)-1-oxaspiro[2.5]octan-6-ol (6.55 g, 23.20 mmol) was mixed in DMF (50 mL) to give a colorless solution. Diethyl vinylphosphonate (4.28 mL, 27.8 mmol) and KOH (3.90 g, 69.6 mmol) were added and the reaction mixture was left to stir for 30 minutes at room temperature. The product was then decanted away from undissolved KOH, diluted with water (200 mL) and extracted with EtOAc (2×300 mL). The combined extracts were concentrated and purified by preparative HPLC, eluting with 35-75% CH$_3$CN in 10 mM aq NH$_4$OH. The pure fractions were combined, concentrated to about half the original volume, and then extracted with Et$_2$O (2×500 mL). The organics were washed with water and concentrated to yield the title compound as a viscous clear oil (5 g, 48%). $^1$H NMR (400 MHz, CD$_3$OD) δ ppm 0.90-1.03 (m, 1H), 1.19 (s, 3H), 1.32 (td, J=7.07, 1.26 Hz, 6H), 1.62-1.69 (m, 4H), 1.76 (s, 3H), 1.97-2.08 (m, 2H), 2.12-2.25 (m, 4H), 2.31 (d, J=7.07 Hz, 1H), 2.53 (d, J=4.29 Hz, 1H), 2.60 (t, J=6.32 Hz, 1H), 2.95 (d, J=4.29 Hz, 1H), 3.44 (s, 3H), 3.60 (dd, J=11.12, 2.53 Hz, 1H), 3.74-3.89 (m, 2H), 4.07-4.16 (m, 5H), 5.20-5.27 (m, 1H). [M+H]$^+$ calc'd for C$_{22}$H$_{40}$O$_7$P, 447.25; found 447.4.

TABLE 1 lists MetAP2 inhibition for some of the compounds shown in the examples, where larger pIC$_{50}$ and pEC$_{50}$ values represent higher potency. The compounds shown in TABLE 1 were tested in accordance with the enzyme assay (pIC$_{50}$) described in the specification beginning at page 35, in which the MetAP2 enzyme is complexed with cobalt or manganese ions, and in accordance with the cellular assay (pEC$_{50}$) described in the specification beginning at page 36.

TABLE 1

MetAP2 Inhibition

| Example No. | MetAP2 Co pIC$_{50}$ | MetAP2 Mn pIC$_{50}$ | MetAP2 Cell pEC$_{50}$ |
|---|---|---|---|
| 1 | 7.35 | 6.7 | 8.32 |
| 2 | — | — | 8.18 |
| 3 | — | — | — |
| 4 | — | — | 8.46 |
| 5 | 7.01 | — | 8.21 |

TABLE 2 lists body weight loss (BWL) in mice following treatment with some of the compounds shown in the examples. The compounds shown in TABLE 2 were tested in accordance with the BWL protocol described in the specification beginning at page 36, using the dose, dosing regimen (frequency), and treatment duration indicated in table.

TABLE 2

Body Weight Loss (BWL) in Mice

| Example No. | Dose | Frequency | Duration | BWL % |
|---|---|---|---|---|
| 1 | 3 mg/kg | once daily | 28 days | 18 |
| 5 | 1 mg/kg | once daily | 28 days | 18 |

TABLE 3 lists glycated hemoglobin (GHb) and plasma glucose (PG) levels in KKA$^y$ mice after a 4-week treatment with the compound shown in Example 1. The study was conducted in accordance with the protocol described in the specification beginning at page 37, using the dose indicated in table. Values are indicated by mean±standard deviation of 8 animals in each group.

TABLE 3

Hypoglycemic Activity in Mice

| Group | Dose | GHb % | PG mg/dL |
|---|---|---|---|
| Control | — | 6.8 ± 0.4 | 436.6 ± 64.4 |
| Example 1 | 10 mg/kg | 5.6 ± 0.4† | 296.5 ± 77.4† |

†$p < 0.025$ vs. control by a one-tailed Williams' test.

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A method for treating a disease, disorder or condition in a subject, the method comprising administering to the subject a compound of Formula 1,

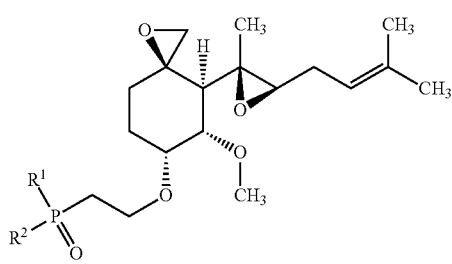

a stereoisomer thereof or a pharmaceutically acceptable salt of the compound or stereoisomer, wherein:

$R^1$ and $R^2$ are each independently selected from phenyl, $C_{3-5}$ heteroaryl, —$OR^4$, and —$N(R^4)R^5$, wherein each phenyl and $C_{3-5}$ heteroaryl is independently substituted with from 0 to 3 $R^a$, and each $C_{3-5}$ heteroaryl has 5 or 6 ring atoms of which 1 or 2 are heteroatoms independently selected from N, O, and S;

each $R^a$ is independently selected from halo, —CN, $R^3$, and $R^4$;

each $R^3$ is independently selected from —$OR^4$, —$N(R^4)R^5$, —$NR^4C(O)R^6$, —$NR^4C(O)OR^5$, —$C(O)OR^4$, —$C(O)N(R^4)R^5$, —$C(O)N(R^4)OR^5$, —$C(O)N(R^4)S(O)_2R^6$, —$N(R^4)S(O)_2R^6$, —$SR^4$, —$S(O)R^6$, —$S(O)_2R^6$, and —$S(O)_2N(R^4)R^5$;

each $R^4$ and $R^5$ is independently selected from
(a) $C_{1-6}$ alkyl, $C_{2-6}$ alkenyl, and $C_{2-6}$ alkynyl, each substituted with from 0 to 3 $R^b$, and
(b) $C_{3-8}$ cycloalkyl-$(CH_2)_m$—, $C_{2-6}$ heterocyclyl-$(CH_2)_m$—, $C_{6-14}$ aryl-$(CH_2)_m$—, and $C_{1-9}$ heteroaryl-$(CH_2)_m$—, each substituted with from 0 to 3 $R^c$;

each $R^6$ is independently selected from
(a) $C_{1-6}$ alkyl, which is substituted with from 0 to 3 $R^b$, and
(b) $C_{3-8}$ cycloalkyl-$(CH_2)_m$—, $C_{2-6}$ heterocyclyl-$(CH_2)_m$—, $C_{6-14}$ aryl-$(CH_2)_m$—, and $C_{1-9}$ heteroaryl-$(CH_2)_m$—, each substituted with from 0 to 3 $R^d$;

each $R^b$ is independently selected from halo, —CN, and $R^7$;

each $R^c$ is independently selected from
(a) halo, —CN, and $R^7$, and
(b) $C_{1-6}$ alkyl, $C_{2-6}$ alkenyl, and $C_{2-6}$ alkynyl, each substituted with from 0 to 3 $R^b$;

each $R^d$ is independently selected from
(a) halo, —CN, and $R^7$, and
(b) $C_{1-6}$ alkyl, which is substituted with from 0 to 3 $R^b$;

each $R^7$ is independently selected from —$OR^8$, —$N(R^8)R^9$, —$NR^8C(O)R^9$, —$NR^8C(O)OR^9$, —$C(O)OR^8$, —$C(O)N(R^8)R^9$, —$C(O)N(R^8)OR^9$, —$C(O)N(R^8)S(O)_2R^9$, —$N(R^8)S(O)_2R^9$, —$SR^8$, —$S(O)R^8$, —$S(O)_2R^8$, and —$S(O)_2N(R^8)R^9$;

each $R^8$ and $R^9$ is independently selected from $C_{1-6}$ alkyl, $C_{3-8}$ cycloalkyl-$(CH_2)_m$—, and $C_{2-6}$ heterocyclyl-$(CH_2)_m$—, each substituted with from 0 to 3 substituents independently selected from halo and —CN; and each m is independently selected from 0, 1, 2, 3, and 4;

wherein each heteroaryl moiety listed in $R^4$, $R^5$, and $R^6$ independently has from 1 to 4 heteroatoms independently selected from N, O, and S, and each heterocyclyl moiety listed in $R^4$, $R^5$, $R^6$, and $R^8$ independently has from 1 to 4 heteroatoms independently selected from N, O, and S; and wherein the disease, disorder or condition is selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, atherosclerosis, and Prader-Willi syndrome.

2. The method according to claim 1, wherein $R^1$ and $R^2$ are each independently selected from phenyl and $C_{3-5}$ heteroaryl, and each phenyl and $C_{3-5}$ heteroaryl is independently substituted with from 0 to 3 $R^a$.

3. The method according to claim 1, wherein each $R^1$ and $R^2$ is independently selected from phenyl and $C_{3-5}$ heteroaryl, each $C_{3-5}$ heteroaryl having 5 ring atoms, wherein each phenyl and $C_{3-5}$ heteroaryl is independently substituted with from 0 to 3 $R^a$.

4. The method according to claim 1, wherein each $R^1$ and $R^2$ is independently selected from phenyl and $C_{3-5}$ heteroaryl, each $C_{3-5}$ heteroaryl having 6 ring atoms, wherein each phenyl and $C_{3-5}$ heteroaryl is independently substituted with from 0 to 3 $R^a$.

5. The method according to claim 1, wherein each $R^1$ and $R^2$ is independently selected from phenyl and $C_{3-5}$ heteroaryl, each $C_{3-5}$ heteroaryl is pyridinyl, and each phenyl and $C_{3-5}$ heteroaryl is independently substituted with from 0 to 3 $R^a$.

6. The method according to claim 1, wherein $R^1$ and $R^2$ are both $C_{3-5}$ heteroaryl, and each $C_{3-5}$ heteroaryl is independently substituted with from 0 to 3 $R^a$.

7. The method according to claim 1, wherein $R^1$ and $R^2$ are both phenyl, and each phenyl is independently substituted with from 0 to 3 $R^a$.

8. The method according to claim 1, wherein:
each $R^a$ is independently selected from halo, —CN, $R^3$, and $R^4$;
each $R^3$ is independently selected from —N($R^4$)$R^5$, —N$R^4$C(O)$R^6$, and —C(O)N($R^4$)$R^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, which is substituted with from 0 to 3 $R^c$;
each $R^6$ is independently selected from
  (a) $C_{1-6}$ alkyl, which is substituted with from 0 to 3 $R^b$, and
  (b) $C_{6-14}$ aryl-(CH$_2$)$_m$—, which is substituted with from 0 to 3 $R^d$;
each $R^b$ is independently selected from halo, —CN, and $R^7$;
each $R^c$ and $R^d$ is independently selected from
  (a) halo, —CN, and $R^7$, and
  (b) $C_{1-6}$ alkyl, which is substituted with from 0 to 3 $R^b$;
each $R^7$ is independently selected from O$R^8$, —N($R^8$)$R^9$, —N$R^8$C(O)$R^9$, and —C(O)N($R^8$)$R^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and CN.

9. The method according to claim 1, wherein:
each $R^a$ is independently selected from halo, —CN, $R^3$, and $R^4$;
each $R^3$ is independently selected from —O$R^4$ and —N($R^4$)$R^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, wherein the $C_{6-14}$ aryl moiety is phenyl substituted with from 0 to 3 substituents independently selected from $R^b$ and $C_{1-6}$ alkyl, and each $C_{1-6}$ alkyl is independently substituted with from 0 to 3 $R^b$;
each $R^b$ is independently selected from halo, —CN, and $R^7$;
each $R^c$ is independently selected from
  (a) halo, —CN, and $R^7$, and
  (b) $C_{1-6}$ alkyl, which is substituted with from 0 to 3 $R^b$;
each $R^7$ is independently selected from —O$R^8$ and —N($R^8$)$R^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and —CN.

10. The method according to claim 1, wherein:
each $R^a$ is independently selected from halo, —CN, $R^3$, and $R^4$;
each $R^3$ is independently selected from —O$R^4$ and —N($R^4$)$R^5$;
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, wherein the $C_{6-14}$ aryl moiety is phenyl substituted with from 0 to 3 substituents independently selected from $R^b$ and $C_{1-6}$ alkyl, and each $C_{1-6}$ alkyl is independently substituted with from 0 to 3 $R^b$;
each $R^b$ is independently selected from halo and —CN; and
each $R^c$ is independently selected from halo, —CN, and $C_{1-6}$ alkyl substituted with from 0 to 3 $R^b$.

11. The method according to claim 1, wherein:
each W is independently selected from halo, —CN, $R^3$, and $R^4$;
each $R^3$ is independently selected from —O$R^4$ and —N($R^4$)$R^5$;
each $R^4$ and $R^5$ is independently selected from $C_{1-6}$ alkyl substituted with from 0 to 3 $R^b$; and
each $R^b$ is independently selected from halo and —CN.

12. The method according to claim 1, wherein $R^a$ is absent.

13. The method according to claim 1, wherein $R^1$ and $R^2$ are each independently selected from —O$R^4$ and —N($R^4$)$R^5$.

14. The method according to claim 1, wherein $R^1$ and $R^2$ are both —O$R^4$.

15. The method according to claim 13, wherein:
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, which is substituted with from 0 to 3 W;
each $R^b$ is independently selected from halo, —CN, and $R^7$;
each $R^c$ is independently selected from
  (a) halo, —CN, and $R^7$, and
  (b) $C_{1-6}$ alkyl substituted with from 0 to 3 $R^b$;
each $R^7$ is independently selected from —O$R^8$, —N($R^8$)$R^9$, —N$R^8$C(O)$R^9$, and —C(O)N($R^8$)$R^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and —CN.

16. The method according to claim 13, wherein:
each $R^4$ and $R^5$ is independently selected from
  (a) $C_{1-6}$ alkyl, which is substituted with from 0 to 3 $R^b$, and
  (b) $C_{6-14}$ aryl-(CH$_2$)$_m$—, wherein the $C_{6-14}$ aryl moiety is phenyl substituted with from 0 to 3 $R^c$;
each $R^b$ is independently selected from halo, —CN, and $R^7$;
each $R^c$ is independently selected from
  (a) halo, —CN, and $R^7$, and
  (b) $C_{1-6}$ alkyl substituted with from 0 to 3 $R^b$;
each $R^7$ is independently selected from —O$R^8$ and —N($R^8$)$R^9$; and
each $R^8$ and $R^9$ is independently selected from $C_{1-6}$ alkyl and $C_{3-8}$ cycloalkyl-(CH$_2$)$_m$—, each substituted with from 0 to 3 substituents independently selected from halo and —CN.

17. The method according to claim 1, wherein:
each $R^4$ and $R^5$ is independently selected from
  (a) $C_{1-6}$ alkyl, which is substituted with from 0 to 3 $R^b$, and (b) C$_{6-14}$ aryl-(CH$_2$)$_m$—, wherein the C$_{6-14}$ aryl moiety is phenyl substituted with from 0 to 3 R$^c$;
each R$^b$ is independently selected from halo and —CN; and
each R$^c$ is independently selected from halo, —CN, and C$_{1-6}$ alkyl, which is substituted with from 0 to 3 R$^b$.

18. The method according to claim 13, wherein:
each R$^4$ and R$^5$ is independently selected from C$_{1-6}$ alkyl substituted with from 0 to 3 R$^b$; and
each R$^b$ is independently selected from halo and —CN.

19. The method according to claim 13, wherein:
each R$^4$ and R$^5$ is independently selected from C$_{1-3}$ alkyl substituted with from 0 to 3 R$^b$; and
each R$^b$ is independently selected from halo and —CN.

20. The method according to claim 13, wherein:
each R$^4$ and R$^5$ is independently selected from methyl and ethyl, each substituted with from 0 to 3 R$^b$; and
each R$^b$ is independently selected from halo and —CN.

21. The method according to claim 13, wherein:
each R$^4$ and R$^5$ is independently methyl substituted with from 0 to 3 R$^b$; and
each R$^b$ is independently selected from halo and —CN.

22. The method according to claim 13, wherein:
each R$^4$ and R$^5$ is independently ethyl substituted with from 0 to 3 R$^b$; and
each R$^b$ is independently selected from halo and —CN.

23. The method according to claim 1, wherein R$^d$ is absent.

24. The method according to claim 1, wherein m is 0.

25. The method according to claim 1, wherein R$^c$ is absent.

26. The method according to claim 1, wherein R$^b$ is absent.

27. The method according to claim 1, wherein the compound is selected from the following compounds:
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)diphenylphosphine oxide;
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)di-p-tolylphosphine oxide;
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)bis(4-(trifluoromethyl)phenyl)phosphine oxide;
dimethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate;
diethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate;
a stereoisomer of any one of the aforementioned compounds; and
a pharmaceutically acceptable salt of any one of the aforementioned compounds or stereoisomers.

28. The method according to claim 1, wherein the compound is selected from the following compounds:
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)diphenylphosphine oxide;
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)di-p-tolylphosphine oxide;
(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)bis(4-(trifluoromethyl)phenyl)phosphine oxide;
dimethyl(2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate;
diethyl (2-(((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)ethyl)phosphonate; and
a pharmaceutically acceptable salt of any one of the aforementioned compounds.

29. The method according to claim 1, wherein the compound is represented by the structure:

30. The method according to claim 1, wherein the compound is represented by the structure:

31. The method according to claim 1, wherein the compound is represented by the structure:

32. The method according to claim 1, wherein the compound is represented by the structure:

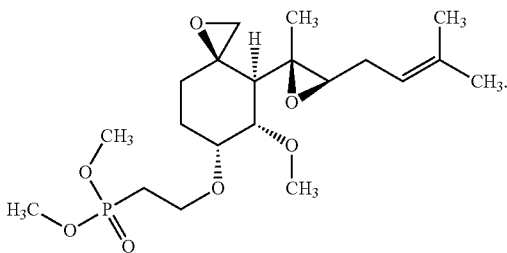 [SMILES: CO[C@@H]1[C@H](OCCP(=O)(OC)OC)CC[C@]2(CO2)[C@H]1[C@@]1(C)O[C@@H]1CC=C(C)C]

33. The method according to claim 1, wherein the compound is represented by the structure:

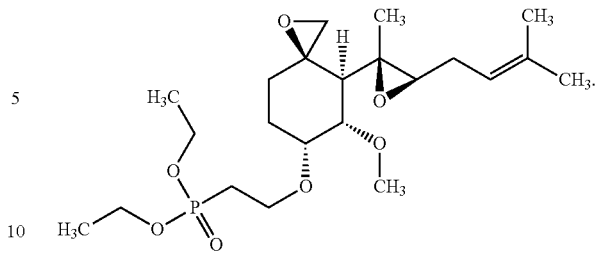

34. The method according to claim 1, further comprising administering at least one additional pharmacologically active agent.

35. The method according to claim 34, wherein the additional pharmacologically active agent is selected from insulin, buformin, metformin, phenformin, pioglitazone, rosiglitazone, acetohexamide, chlorpropamide, tolazamide, tolbutamide, gliclazide, glimepiride, glipizide, glyburide, nateglinide, repaglinide, acarbose, miglitol, exenatide, liraglutide, taspoglutide, alogliptin, linagliptin, saxagliptin, sitagliptin, vildagliptin, pramlinitide, orlistat, atorvastatin, fluvastatin, lovastatin, mevastatin, pitavastatin, pravastatin, rosuvastatin, simvastatin, niacin, bezafibrate, ciprofibrate, clofibrate, fenofibrate, gemfibrozil, cholestyramine, colesevelam, colestipol, and ezetimibe.

* * * * *